US00PP23872P2

(12) United States Plant Patent
Hansen

(10) Patent No.: US PP23,872 P2
(45) Date of Patent: Sep. 3, 2013

(54) ***BAPTISIA* PLANT NAMED 'DUTCH CHOCOLATE'**

(50) Latin Name: ***Baptisia*×hybrid**
Varietal Denomination: Dutch Chocolate

(75) Inventor: Hans Andrew Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 109 days.

(21) Appl. No.: 13/374,347

(22) Filed: Dec. 22, 2011

(51) Int. Cl.
*A01H 5/00* (2006.01)

(52) U.S. Cl.
USPC ..... Plt./263.1; Plt./226

(58) Field of Classification Search
USPC ..... Plt./263.1, 226
See application file for complete search history.

*Primary Examiner* — Susan McCormick Ewoldt
(74) *Attorney, Agent, or Firm* — Penny J. Aguirre

(57) ABSTRACT

A new cultivar of interspecific *Baptisia*, 'Dutch Chocolate', characterized by its purple-brown flowers that are held on erect flower stems, its densely branched, mounded and compact plant habit, its vigorous growth rate and its hardiness to U.S.D.A. Zones 4 to 9.

2 Drawing Sheets

Botanical classification: *Baptisia*×hybrid.
Cultivar designation: 'Dutch Chocolate'.

BACKGROUND OF THE INVENTION

The present invention relates to a new and distinct cultivar of hybrid *Baptisia* plant, botanically known as *Baptisia*× hybrid 'Dutch Chocolate' and will be referred to hereafter by its cultivar name, 'Dutch Chocolate'. The new cultivar represents a new false indigo, an herbaceous perennial grown for garden and landscape use.

The new invention arose from an ongoing controlled breeding program in Waseca, Minn. that was established by the Inventor in 1998 using superior selections of numerous species of *Baptisia* with the goal of developing unique color forms and plant habits of *Baptisia* suited for general garden and landscape use.

'Dutch Chocolate' derived from a cross made in 2003 (cross no. 03-40A) between an unnamed selection of *Baptisia minor* as the female parent and an unnamed plant of *Baptisia sphareocarpa* as the male parent. 'Dutch Chocolate' was selected in 2007 as a single unique plant amongst the progeny of the cross.

Asexual reproduction of the new cultivar was first accomplished by stem cuttings in early June of 2008 in Zeeland, Mich. under the direction of the Inventor. The characteristics of this cultivar have been determined to be stable and are reproduced true to type in successive generations.

SUMMARY OF THE INVENTION

The following traits have been repeatedly observed and represent the characteristics of the new cultivar as observed for four years in Waseca, Minn. These attributes in combination distinguish 'Dutch Chocolate' from other varieties of *Baptisia* known to the Inventor.

1. 'Dutch Chocolate' exhibits flowers that are purple-brown in color, a characteristic that has not been observed in any species or hybrid known to the Inventor.
2. 'Dutch Chocolate' exhibits foliage that is blue-green in color.

3. 'Dutch Chocolate' has an upright and uniform plant habit.
4. 'Dutch Chocolate' produces flower stems produced above the mound of foliage.
5. 'Dutch Chocolate' is hardy in U.S.D.A. Zones 4 to 8.

In comparison to the female parent, *Baptisia minor*, 'Dutch Chocolate' has purple-brown flowers whereas *Baptisia minor* has blue flowers. 'Dutch Chocolate' also has an upright habit, larger flowers, and longer inflorescences. In comparison to the male parent, *Baptisia sphaerocarpa*, 'Dutch Chocolate' has purple-brown flowers whereas *Baptisia sphaerocarpa* has yellow flowers and 'Dutch Chocolate' has a greater quantity of flower spikes and matures to a more compact size. 'Dutch Chocolate' has seedpods that are intermediate in characteristics between the two parents, but are more similar to the seedpods of the male parent in their rounded shape, color, and thickness. The closest comparison cultivar is *Baptisia* 'Twilite' (U.S. Plant Pat. No. 19,011), which is also an interspecific hybrid, however 'Twilite' has a larger plant habit and violet-lavender colored flowers with a yellow keel. 'Dutch Chocolate' may also be compared to 'Chocolate Chip' (not patented), an additional interspecific hybrid, however 'Chocolate Chip' has inflorescences that arch at a 45° angle midway at the bloom sequence and has a larger, more open plant habit and form.

BRIEF DESCRIPTION OF THE DRAWINGS

The accompanying colored photographs illustrate the overall appearance and distinct characteristics of the new *Baptisia*. The photographs were taken of plants and plant parts of a plant five years in age as grown outdoors in Waseca, Minn.

The photograph in FIG. 1 is a view of a plant of 'Dutch Chocolate' in bloom and illustrates the flower aspect.

Figure 1:
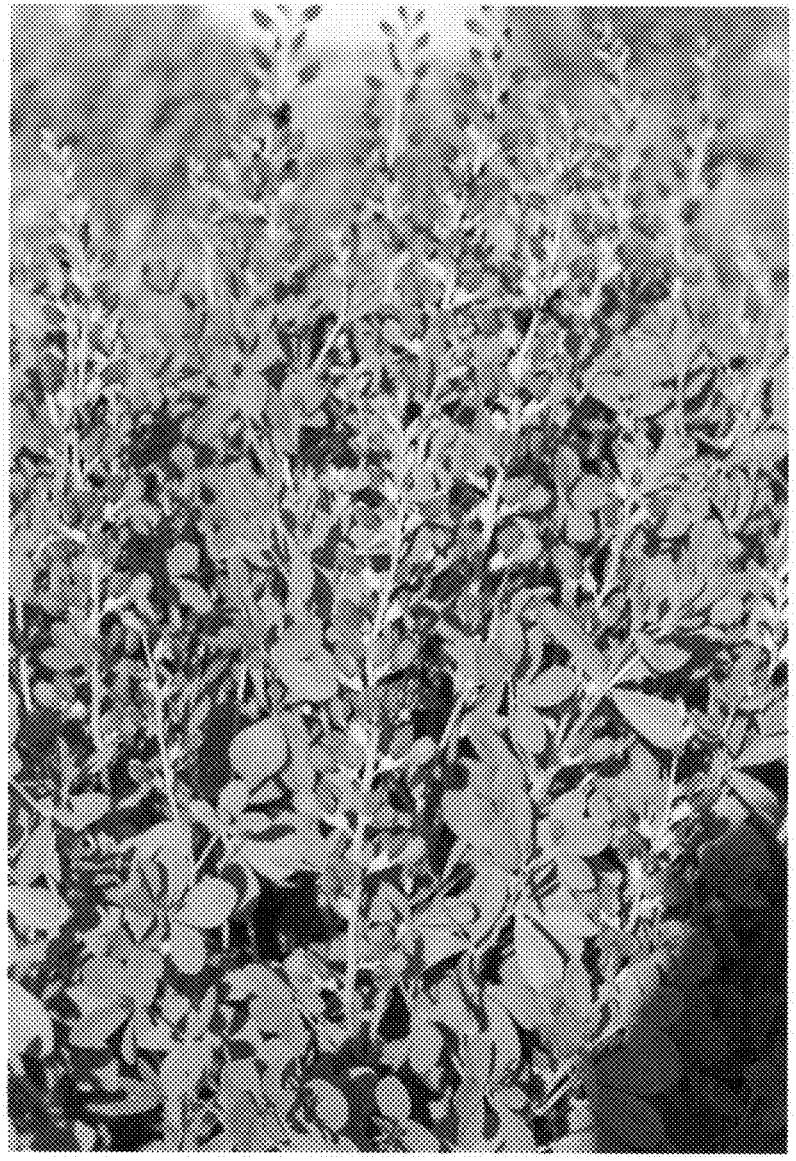
Figure 2:
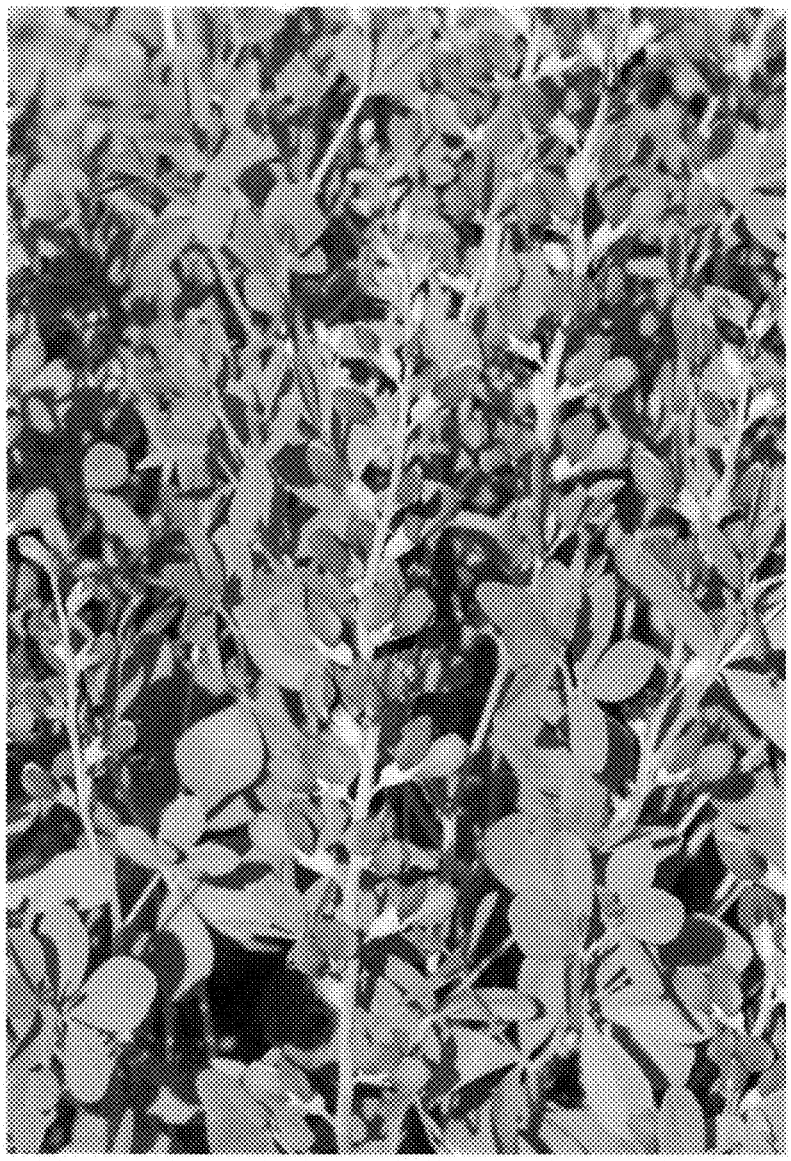

The photograph in FIG. 2 is of a close-up view of an inflorescence of 'Dutch Chocolate'.

The colors in the photographs may differ slightly from the color values cited in the detailed botanical description, which accurately describe the colors of the new *Baptisia*.

DETAILED BOTANICAL DESCRIPTION OF THE PLANT

The following is a detailed description of 5 year-old plants of the new cultivar as grown outdoors in a trial plot in Waseca, Minn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Early June through late June in Waseca, Minn. (June 10-June 26).

*Plant habit.*—Densely foliaged, mound-shaped.

*Height and spread.*—Reaches 60 cm width and 85 cm in height.

*Hardiness.*—U.S.D.A. Zones 4 to 8.

*Culture.*—Prefers well drained to medium moist soils in full sun, tolerant to lean soils and drought.

*Diseases and pests.*—No susceptibility to diseases or pests has been observed.

*Root description.*—Deep rooted, fibrous.

Growth and propagation:

*Propagation.*—Stem cuttings, tissue culture is also possible.

*Growth rate.*—Vigorous.

Stem description:

*Branch habit.*—Very densely branched; average of 35 branches with an average of 3 secondary branches, and 2 tertiary branches per secondary branch, foliage starts at an average of 17 cm from base.

*Stem size.*—Main stem; average of 85 cm (including peduncle) in length and 6 mm in width (9 mm at base), secondary; average of 32 cm in length (including peduncle) and 4 mm in width, tertiary (non-flowering); an average of 10 cm in length and 2 mm in width.

*Stem shape.*—Oval.

*Stem color.*—144A.

*Stem surface.*—Hairless, satiny but slightly glaucous, fine vertical ridges.

*Stem aspect.*—Upright.

*Stem strength.*—Strong.

Foliage description:

*Leaf shape.*—Fan-shaped in overall outline.

*Leaf division.*—3-palmate.

*Leaf internode.*—Foliage begins 17 cm from base, an average of 6.5 cm on main stem and 6 cm on secondary branches.

*Leaf size.*—About 3.8 cm in length and 7 cm in width when mature.

*Leaf quantity.*—About 30 per stem.

*Leaflet shape.*—Oblanceolate.

*Leaflet base.*—Cuneate.

*Leaflet apex.*—Retuse.

*Leaflet venation.*—Pinnate pattern, not conspicuous, color matches leaflet color on the upper and lower surface with the mid rib of lower surface and base of upper surface 144C.

*Leaflet margins.*—Entire.

*Leaf attachment.*—Petiolate.

*Leaf arrangement.*—Alternate.

*Leaflet surface.*—Glabrous and slightly glaucous on upper and lower surface with lower surface more glaucous.

*Leaflet color.*—Newly expanded upper and lower surface; blend of 147A and 147B, mature upper and lower surface; blend of 147A and 191A.

*Leaflet size.*—An average of 3.8 cm in length and 2 cm in width.

*Petioles.*—Average of 2.5 mm in length and 1.5 mm in width, clasping to stem at mature nodes, 144A in color, surface is glabrous and satiny.

*Stipules.*—Narrowly lanceolate in shape, not present on all stems, held upright to horizontal to stem, base is truncate to stem, apex is apiculate, average of 1.8 cm in length 4 mm in width on mature leaves, color is 147A on upper surface and lower surface and 146D near base.

Flower description:

*Inflorescence type.*—Terminal racemes of pea-like flowers on main stems and secondary stems, blooms from the base to the apex.

*Inflorescence size.*—Main stems; an average of 30 cm in length and 5 cm in width in mid section.

*Lastingness of inflorescence.*—About 25 days.

*Flower size.*—About 2.5 cm in depth and about 1.8 cm in diameter.

*Flower fragrance.*—Faint.

*Flower number per inflorescence.*—Average of 39.

*Peduncle.*—Oval in shape, up to 32 cm in length and an average of 3 mm in width, 144A in color, surface is glabrous, satiny and slightly glaucous, flower internode length averages about 5 mm.

*Petiole.*—About 4 mm in length, and 1.5 mm in width, oval in shape, 146A in color, glabrous and satiny surface.

*Flower buds.*—Kidney-shaped, about 2.3 cm in length and 9 mm in width, color of petal N92A suffused with 199A with exposed keel portion 1C suffused with 144C near base, calyx portion same as open flowers.

*Flower type.*—Papilionaceous, held at about a 45° angle.

*Calyx.*—Campanulate, about 9 mm in length and 6 mm in diameter, surface is puberulent with margin of infused tips villose, color is a blend of 146A, 146B and 146C.

*Sepals.*—5, fused with the exception of apex of each, free portion is triangular in shape 2 mm in width and 3 mm in depth with an acute apex, color is a blend of 146A, 146B and 146C on both surfaces.

*Corolla features.*—Papilionaceous (4 segments) with a keel, a banner and 2 lateral wings, lateral wings; obelliptic in shape, flared to expose keel, about 2.2 cm in length and 9 mm in width, color outer surface; N92A suffused with 199A, color inner surface; a blend of 92A and N77C with the basal portion 150C, rounded apex, oblique base, keel; only partially visible, comprised of 2 segments surrounding reproductive organs, oblong (slightly oblique) in shape with rounded apex and oblique base, 2 cm in length and 9 mm in width, upper surface and lower surface are 1C in color becoming 150B to 144C and suffused at apex with N77A at base, banner; orbicular in shape and partially reflexed, about 1.6 cm in length and 1.2 cm in width when reflexed, upper and lower surface is N92A suffused with 199A in color with the basal portion 1A, and midrib 150B, all sections fade to a blend of N92D and 199C, apex is rounded with a single notch, surface is glabrous and margins are on all sections entire.

*Receptacle.*—Disk-shaped, gelatinous, 146C in color, about 2 mm in diameter and 1.5 mm in depth.

Reproductive organs:

*Gynoecium.*—1 Pistil, about 1.7 cm in length; style is 144C in color and 1 cm in length; stigma minute, too small to read color, ovary is superior with a stipe, 144A in color, 5 mm in length and 1.5 mm in width; stipe is 144B in color, 3 mm in length and 1 mm in width.

*Androcoecium.*—10 stamens, not united, 1.6 cm in length, filament is 1.3 cm in length, 0.7 mm in width and 145B in color; anther is dorsifixed, many oval shaped, about 2 mm in length and 1.5 mm in width and 14A in color, pollen is abundant and 17A in color.

*Fruit.*—An inflated pod, technically a legume, globose-oblongoid in shape, an average of 2.5 cm in length and 1.6 cm in width; each with a short beak approximately 1 mm in length stipe 1.5 cm in length 1 mm in width, matures in September to a blend of 200A and N200B on outer surface and 200D on inner surface, interior surface wall glossy, walls are about 1.5 mm in thickness and woody at maturity, Seed; 165A in color, oval with the hilum side more or less straight, seed compressed to flattish, 4 mm in length, 2 mm in width and 2 mm in thickness.

It is claimed:

1. A new and distinct cultivar of *Baptisia* plant named 'Dutch Chocolate' as herein illustrated and described.

* * * * *